United States Patent
Guhl

[11] Patent Number: 5,544,683
[45] Date of Patent: Aug. 13, 1996

[54] SAMPLE FILLING DEVICE

[75] Inventor: Peter Guhl, Karlsruhe, Germany

[73] Assignee: Bruker Analytische Messtechnik GmbH, Germany

[21] Appl. No.: 349,976

[22] Filed: Dec. 6, 1994

[30] Foreign Application Priority Data

Dec. 18, 1993 [DE] Germany ............... 43 43 400.2

[51] Int. Cl.[6] .................................................. G01N 35/06
[52] U.S. Cl. .................. 141/65; 141/69; 141/130; 141/98; 141/284; 141/279; 141/83; 366/124; 366/208; 366/114; 414/21; 414/404; 414/415; 901/6; 422/63; 422/104
[58] Field of Search .................. 141/130, 83, 98, 141/65, 69, 71, 256, 279, 284, 1; 414/404, 415, 420, 21; 222/161, 164–166, 196; 422/63, 67, 99, 104; 901/6; 366/110, 114, 116, 124, 139, 141, 154.2, 185, 208

[56] References Cited

U.S. PATENT DOCUMENTS

| | | | |
|---|---|---|---|
| 2,875,989 | 3/1959 | Toulmin, Jr. | 366/114 |
| 3,654,970 | 4/1972 | Teboul | 141/284 |
| 4,588,300 | 5/1986 | Guy | 366/114 |
| 4,619,336 | 10/1986 | Boyer et al. | |
| 4,632,009 | 12/1986 | Dann | 222/166 X |
| 4,849,175 | 7/1989 | Dupain et al. | 422/63 |
| 4,867,258 | 9/1989 | Narukawa et al. | 141/83 X |
| 5,143,126 | 9/1992 | Boesch et al. | 141/1 |
| 5,209,564 | 5/1993 | Manci et al. | 366/124 |
| 5,363,885 | 11/1994 | McConnell et al. | 141/1 |

FOREIGN PATENT DOCUMENTS

| | | |
|---|---|---|
| 1673523 | 3/1954 | Germany. |
| 2050364 | 6/1972 | Germany. |
| 2326244 | 12/1974 | Germany. |
| 2439586 | 3/1975 | Germany. |
| 3124948 | 3/1982 | Germany. |
| 3517162 | 12/1985 | Germany. |
| 3430170 | 2/1986 | Germany. |
| 2200469 | 8/1988 | United Kingdom. |
| WO90/03834 | 4/1990 | WIPO. |

OTHER PUBLICATIONS

Pytechnology, by Zymark Corp., 422/63, Nov. 17, 1986.
Felder, R. A. et al.: Bots In Health Care, in: Analytical Chemistry, vol. 63, No. 14, Jul. 15, 1991, 741ff.
Mellbin, Göran: Application Of Laboratory Robots In Industrial Automation in: Analytica Chimica Acta, 238 (1990) pp. 71–77.
ISMATEC 93/94 (Company Brochure of Ismatec sa, CH–8152 Glattbrugg, Switzerland).

*Primary Examiner*—J. Casimer Jacyna
*Attorney, Agent, or Firm*—Walter A. Hackler

[57] ABSTRACT

A method and an apparatus for the automatic quantitative filling of powdered or granulated samples for analytic measurement purposes as well as a shaking and holding device for sample substances utilized therefor with which precisely admeasured amounts of the sample substance can be filled into a measuring vessel. The shaking device permits the sample substance to be filled in a continuous, slow and defined flowing stream. The shaking and holding of the sample vessel transpires preferentially pneumatically.

4 Claims, 5 Drawing Sheets

SAMPLE FILLING DEVICE

BACKGROUND OF THE INVENTION

The invention concerns a method and a device for the quantitative filling of powdered or granulated samples for analytic measurement purposes as well as a shaking and holding device suitable therefor.

In order to prepare serial analytic measurements, for example, measurements of nuclear magnetic or electronic spin resonance, it is necessary to, from a plurality of sample containers which are, in general, sample vials having screw tops, sequentially fill measuring vessels, which are, in general, likewise sample vials, with, in each individual case, a precisely, in general, in the milligram range, predetermined and appropriately measured substance amount. Depending on the analytic measurement, a fluid solvent material may be also subsequently added.

In contrast to fluid samples with which the amount to be filled can be precisely measured-off, with powdered samples there is the problem that they can, in general, not be dosed out with a pipette. Pouring out of a sample vessel is hindered by static friction so that a sudden occurrence of much too large an amount often takes place. This also occurs when the sample substance is only slightly clumped or when its surface, when filling, is not smooth.

There is therefore the need for a practical method or device for the automatic quantitative filling of powdered or granulated sample substances for analytic measurement purposes from a sample vessel into a measuring vessel with which a preselected sample amount can be maintained in a reliable fashion.

The purpose of the invention is to present such a method or such a device.

SUMMARY OF THE INVENTION

This purpose, with respect to the method, is achieved by means of a method having the following method steps:

1) by means of a robot grasping arm, an empty measuring vessel is removed from a storage station and placed on a measuring table of an analytic scale;

2) the analytic scale carries out a zero measurement of the empty measuring vessel;

3) the robot grasping arm removes a predetermined sample vessel which contains a selected sample substance and puts same in a shaking and holding device which is located in its starting position;

4) the robot grasping arm grasps the shaking and holding device having the sample vessel and holds same with its opening over the measuring vessel;

5) the shaking and holding device is switched-on;

6) the robot grasping arm turns the sample vessel slowly out of the vertical into a position with which the sample substance runs out of the sample vessel into the measuring vessel and the sample vessel is shaken and held by means of the shaking and holding device;

7) the analysis scale carries out continuous measurements of the weight of the measuring vessel including that of the poured sample substance.

8) when a predetermined weight for the filled sample substance, given as a difference between the current and the zero measurement, is reached, the filling procedure is interrupted by turning the sample vessel back into the vertical and switching-off the shaking and holding device;

9) the shaking and holding device is placed back into its starting position by the robot grasping arm;

10) the sample bottle is removed from the shaking and holding device and dispensed with;

11) the measuring vessel, having the filled amount of sample substance, is transferred by the robot grasping arm to a transfer station for further processing.

In this fashion the purpose of the invention is completely achieved.

By shaking the sample substance during the filling procedure a clogging of the sample substance due to static friction is largely prevented, clumps are broken-up, the surface is levelled and a practically continuous pouring occurs at a slow filling rate. Within limits, this can be regulated by the tilt angle of the sample vessel whereby, by appropriate rotation of the robot grasping arm, the optimum tilt angle from the vertical up to a safety margin can be relatively quickly adjusted and, by means of shaking, the exact value can be slowly adjusted whereby the filling process begins gradually. Prior thereto, a somewhat stronger shaking can be initially carried out to eliminate extensive clumping.

In a preferred embodiment of the invention the shaking and holding device is pneumatic. This has the advantage that pneumatics can be utilized for the shaking as well as for the holding of the sample vessel. In addition, a plurality of analytic measuring apparatuses utilize pneumatic devices for other purposes so that components can possibly assume a double function.

In a particularly preferred embodiment of the method in accordance with the invention, a shaking and holding device having an open hollow cylindrical chamber and a closed chamber is utilized, the chambers being connected by means of a pressure valve whereby, in step 3) of the method, the open chamber partially accepts the sample vessel with close tolerance and, in step 5), the closed chamber is pumped so that the pressure valve periodically opens as a result of the pressure reduction and closes again when the pressure increases, whereby the pressure fluctuations, on the one hand, cause the sample vessel to oscillate and, on the other hand, the resulting average reduced pressure suctions the sample vessel to serve during the rotational motion of step 6) as a holding device.

The relatively close tolerances in fitting the generally cylindrical sample vial sample vessel into the open chamber cause the vessel to be suctioned with significant force and to be securely held even when tilted after the pressure valve is opened. This is also the case when the pressure valve periodically opens and closes at a relatively high frequency (approximately 30 Hz). In the event that, with closed valve, the suction pressure falls to too great an extent, the sample vessel is repeatedly released for short periods of time and begins, under certain circumstances, to slide out of the open chamber under the influence of gravity to be, however, suctioned back again in time and slides back when the valve is opened. In general, this leads to a shaking motion and a secure holding. The suction pressure can, however, also be adjusted to such a strength that the sample vessel is securely held and suctioned at all times. In this case a spring can be installed between the bottom of the open chamber and the bottom of the sample vessel, against which the sample vessel is pressed, and which causes the pressure fluctuations to induce oscillations of the spring together with the sample vessel.

In an embodiment, the pressure valve is a spherical valve having a sphere pressed against the opening by means of a spring. This simple construction satisfies the necessary requirements. Through appropriate adjustment of the suction strength of the pump and of the spring constant, the filling procedure can be optimized for typical sample materials.

A method is, however, particularly preferred, with which the pressure valve constitutes a striking pin penetrating through the opening and pressed by a spring which, during the periodic shaking motion, is in or comes into periodic contact with the bottom of the sample vessel in the open chamber to thereby mechanically amplify the shaking. In this case the pneumatics must primarily only cause the striking pin motion and not that of the sample vessel itself which must only, as before, be securely held. This, in contrast to the version with the spherical valve, leads to a drastic reduction in the gas through-put with maintained shaking effectiveness. It is much simpler, using reduced pump power to superimpose a shaking motion onto the striking pin, which is part of the valve, and to then transfer same to the sample vessel in that the striking pin periodically strikes its bottom or is in constant contact therewith, whereby the sample vessel always remains pressed against the oscillating striking pin due to the constant reduced pressure.

In an embodiment of the invention, the sample vessel and/or the measuring vessel exhibit screw-on lids which are opened and, if appropriate, closed again by the robot gripping arm. In this fashion, a particular sample vessel can be selected from a station having a plurality of samples securely stored in closed sample vessels and the vessel can be opened and closed again. The storage vessel is then available for a possible plurality of further measurements.

The method has particularly advantages when small amounts of sample substances are involved which must be measured very precisely, for example, when the filled sample amount to be weighed is in the range between 10 and 50 mg, preferentially between 10 and 30 mg, having a precision of more than ±3 mg, preferentially ±1 mg.

In this fashion, in particular with continuous measurement series, the sample vessels and/or the measuring vessels are or can be preferentially encoded by means of a bar code, whereby this encoding can preferentially be optically read out with a bar code reader to select and assign predetermined samples.

The purpose of the invention is achieved with respect, to a shaking and holding device comprising a housing having a largely hollow cylindrical open chamber for the partial acceptance, with close tolerance, of the sample vessel, a closed chamber separated from the open chamber by means of a pressure valve which is adapted to open when the pressure is reduced in the closed chamber, and a device for pumping on the closed chamber.

The pumping of the pumping device allows, namely, for the establishment of an operation mode with which the pressure valve periodically opens and closes relatively quickly as a result of which, on the one hand, a sample vessel is securely held in the open chamber by means of the reduced pressure, and on the other hand, a forced oscillation motion is caused by the pressure fluctuations. In this fashion this shaking and holding device can be advantageously utilized to carried out the above mentioned method.

In an embodiment the pressure valve has a bore through the wall separating the two chambers onto which a sphere is pressed by means of a spring within the closed chamber.

Preferentially, a spring is located on the bottom of the open chamber, against which the bottom of the vessel is suctioned and thereby held when the valve is opened. The periodic opening and closing of the valve leads to oscillations of the spring together with sample vessel.

In an further preferred embodiment the pressure valve has a bore through the separation wall between the two chambers against which a striking pin is pressed within the closed chamber by means of a spring to penetrate through the bore into the open chamber and establish mechanical contact with the bottom of the sample vessel therein.

The advantages resulting therefrom have already been discussed above in connection with the method.

In a simplified embodiment the pumping device is a pumping connector on the closed chamber which can be connected to a vacuum pump by means of a pumping conduit.

With reference to the entire filling device the purpose is achieved in that the filling device comprises:

1) at least one robot gripping arm which removes an empty measuring vessel from a storage station and can place same on the receptacle of an analysis scale;

2) an analysis scale to carry out weighing of the measuring vessel with a precision in the milligram region;

3) a shaking and holding device for a sample vessel which can be held by the robot gripping arm over the measuring vessel and rotated;

4) a pump which is connected by means of a pumping conduit to a pumping device and which, in the switched-in state in association with the shaking and holding device, causes the sample vessel to be held and to vibrate;

5) a control device which is connected to the drive of the robot gripping arm, the analysis scale, and the pump into which information concerning the samples to be filled and the sample amounts can be entered and which preferentially is programmed to carry out the method in accordance with the invention.

Further advantages of the invention can be derived from the description and from the accompanying drawing. Likewise the above mentioned features and those which are to be explained in detail below in accordance with the invention can be utilized, in each case, individually or collectively in arbitrary combination. The embodiments mentioned are not to be taken as exhaustive enumeration, rather have exemplary character only.

The invention is represented in the drawing and is explained in greater detail with reference to concrete embodiments.

DESCRIPTION OF THE PREFERRED EMBODIMENT

Figure 1:
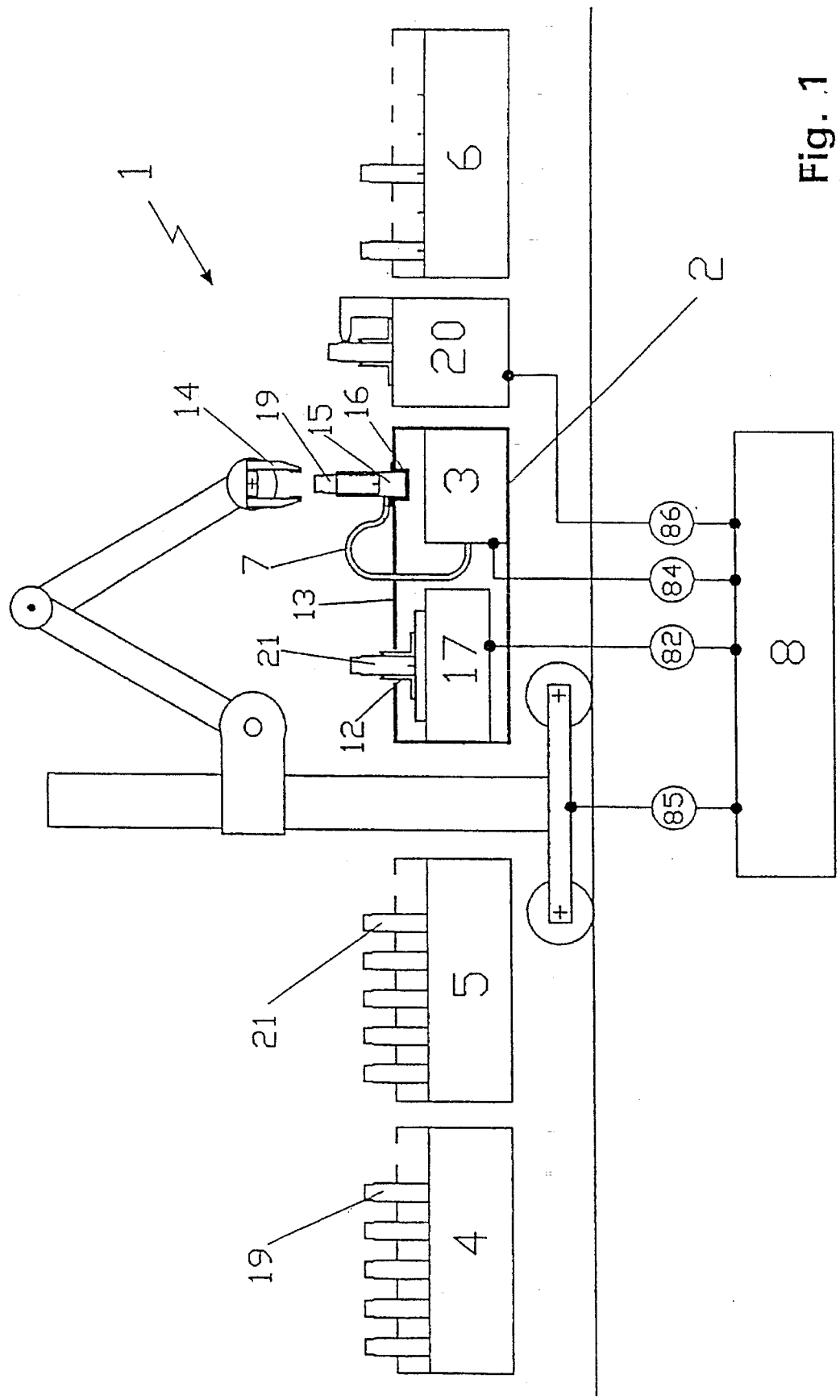
FIG. 1 shows a schematic configuration of the entire filling installation.

FIG. 1 schematically shows, in detail, an overall installation 1 in accordance with the invention. An analysis scale 17 is located in a housing 2 beneath a cover plate 13. A measuring vessel 21 is located on the scale 17 surrounded by a guide 12 which, was transported therein from a supply station 5 with the assistance of a robot grasping arm 14. The robot grasping arm 14 holds a shaking and holding device 15 which has been taken from its resting position in the storage means 16 of the housing 2. A sample vessel 19, which has been taken from a sample station 4, is held by the shaking and holding device 15. The robot grasping arm 14 can pass the measuring vessel 21 to the transfer station 6 after the filling procedure. The shaking and holding device 15 is connected to a pump 3 by means of a flexible pumping conduit 7. A programmable control and analysis device 8 controls the entire filling procedure by means of control and measurement cables 82, 84 and 85 connected to the pump 3, the scale 17, the robot grasping arm 14 as well as to the shaking and holding device 15. The bar codes placed on the samples 19 and the measuring vessels 21 can be read by means of a bar code reader 20, and the vessels can be thereby identified and assigned. The bar code reader is also connected to the control and analysis device 8 by means of cable A measurement process is carried out in the following manner:

All sample vessels 19 are initially located at the sample station 4, all measuring vessels 21 in the supply station 5, and the shaking and holding device 15 in the resting position 16. At the beginning of the filling procedure the control and analysis device 8 causes the robot grasping arm 14 to remove an empty measuring vessel 21 from the supply station 5 and place it in the guide 12 through the cover 13 onto the analysis scale 17. Subsequently, a zero measurement is carried out via the analysis scale 17 and the empty weight of the measuring vessel is stored in the unit 8 via cable 82. The unit 8 accesses stored values for the code of the sample substance or its position in the sample station and causes, via cable 85, the robot grasping arm 14 to grasp the appropriate sample vessel 19, to check the code, if appropriate, in the bar code reader 20 and then to place the sample vessel 19 in the shaking and holding device 15. Subsequently the pump 3 is switched-on, via cable 84, by the control and analysis device 8 as a result of which the sample vessel is securely held in the shaking and holding device 15. By means of the suctional force it is possible to initially keep the shaking function to a small value. The robot grasping arm 14 then grasps the shaking and holding device 15 along with the sample vessel 19 and positions it above the measuring vessel 21. If appropriate, the shaking function is now amplified by changing the pumping force and, via control cable 82, the scale 17 is caused to undertake continuous weighings and to send the measurement result via cable 82 to the control and analysis device 8. The sample vessel 19 is slowly tilted, whereby its opening is located over that of the measuring vessel 21 so that, under continuous shaking, the sample substance begins to run into the measuring vessel 21. The control and analysis device 8 registers an increasing weight and, if appropriate, controls, via cable 85, the tilt angle so that a constant gradual controllable weight increase transpires. As soon as the desired weight is achieved the sample vessel 19 is tilted back by means of the robot grasping arm 14 so that the filling is instantly ended. The weight increase in the measuring vessel 21 is subsequently registered. When same is within a predetermined tolerance (in the mg-range) the value is registered and the filling per se is ended. The shaking and holding device 15 is returned to its resting position 16, the pump 3 is turned-off, the sample vessel 19 is again removed from the shaking and holding device 15 and returned to the sample station 4, and the measuring vessel 21 is moved to the transfer station 6 by the robot grasping arm 14. Prior thereto, if appropriate, a bar code is read-off from the measuring vessel 21 by the bar code reader 20, sent to the control and analysis station 8, and correlated to the actual weight. The apparatus 1 is then ready for the next filling procedure.

Should the weight be too low, subsequent filling can take place. If the weight is excessive it is possible to either set-off an alarm, set aside the measuring vessel 21, and fill a new empty one, or for the sample vessel 19 to be set aside, the shaking and holding device is to be brought into the resting position 16, the measuring vessel 21 to be grasped and subsequently the sample substance, at least partially, filled back into the sample vessel 19 or into a disposal vessel. This process does not require precision weighing. Subsequently, the filling can be attempted once more. With repeated failures or when the desired weight is not achieved (an empty sample vessel) an alarm is, in any event, issued. In the event of automatic serial measurements one can go to the next substance and store the aborted experiment as such.

With sample and measuring vessels having a screw lid it is possible for the robot grasping arm 14 to first unscrew and then screw closed the vessel before and after the filling procedure, respectively.

Clearly, the above mentioned individual step sequence can be varied within reasonable limits or complemented by additional steps such a checks by readouts of sensors or the like.

Figure 2:
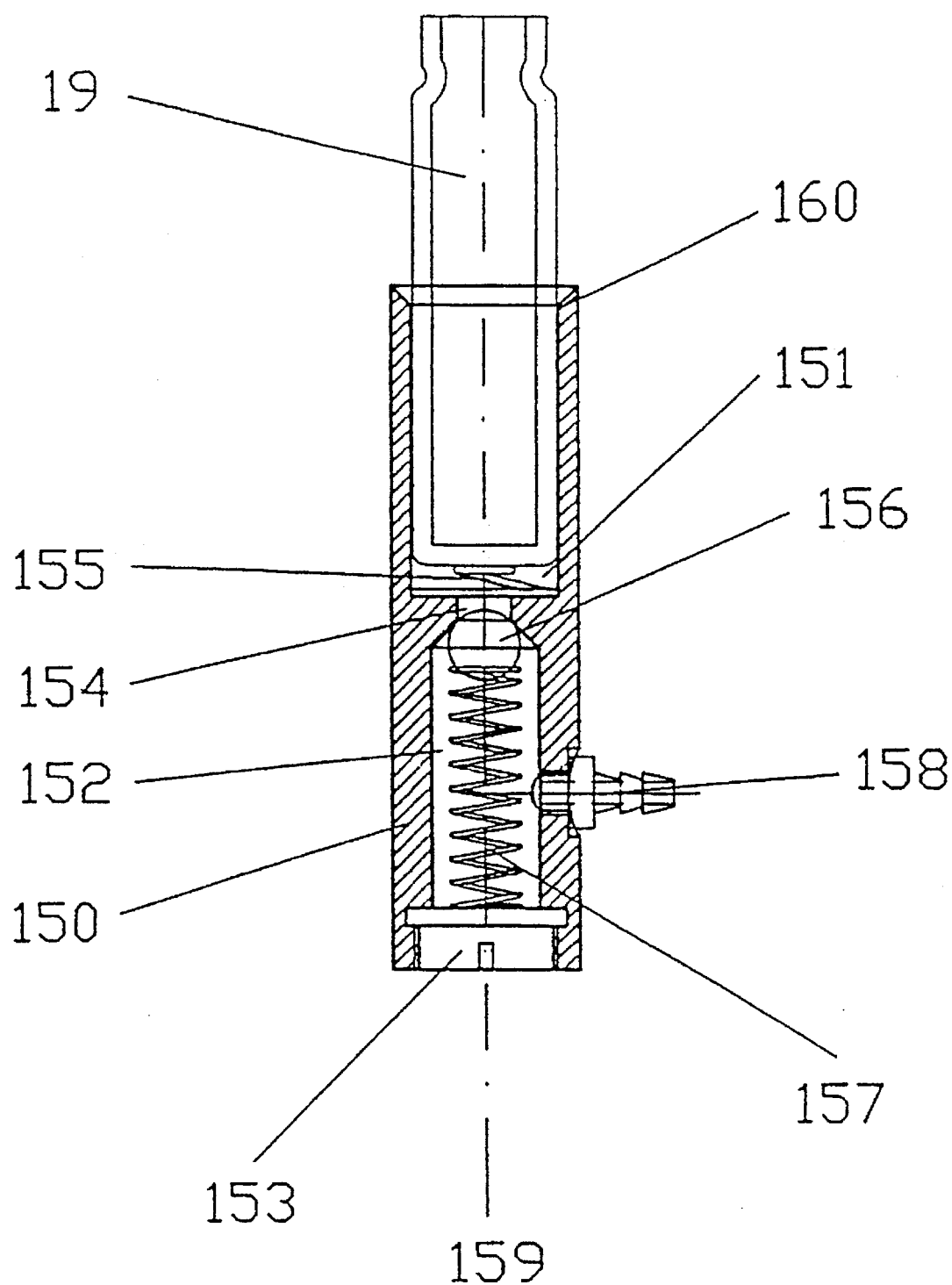
FIG. 2 shows a detailed view of a first embodiment of a shaking and holding device.

FIG. 2 shows a section through a first embodiment of a shaking and holding device 15 in accordance with the invention.

A hollow cylindrical open first chamber 151 and a largely hollow cylindrical second chamber 152, which is closed by means of a lid 153 are located in a largely cylindrical housing 150. The closed chamber 152 is conical on one side and maps into a bore 154 leading to the bottom of the open chamber 151. A cylindrical sample vial 19 is placed, with close tolerance, in the open chamber 151 so that only a small ring-shaped gap 160 remains between the outer wall of the sample vial 19 and the inner wall of the open chamber 151. A first simple spiral spring 155, fixed to the bottom of the chamber, is located between the bottom of the sample vial 19 and the bottom of the open chamber 151. The bore 154 is closed by means of a metal sphere 156 which is pressed by means of a second spiral spring 157 in the closed chamber 152 onto the bore 154. A feed-through having hose stem 158 leads from the outside into the closed chamber 152. A connecting tube 7 can be attached via the hose stem to a suction pump 3 (compare FIG. 1).

When reduced pressure occurs in chamber 152 (produced by the suction pump 3), the pressure valve formed by the bore 154, the sphere 156, and the spring 157 opens since atmospheric pressure is present in the opened chamber 151 which then pushes the sphere 156 against the spring 157 into the chamber 152. In this fashion the sample vial 19 is also suctioned towards the bore 154 and the spring 155 is sprung to a certain extent. Air, however, also enters via the now open bore 154 through the ring gap 160 from the outside. In this fashion the reduced pressure in the chamber 152 is once more reversed. The valve closes again, i.e. the spring 152 relaxes and the sphere 156 closes the bore 154. The reduced pressure on the bottom of the opened chamber 151 is rapidly reversed by the air flowing through the ring-shaped gap, the spring 155 is relaxed and the sample vial 19 begins to move somewhat in a direction out of the chamber 151. Since, however, the pump continuous to suction the feed-through 158, reduced pressure once more occurs in the closed chamber 152 and the entire process starts again from the beginning. In general, the sample vial exercises an oscillation in the open chamber along the cylinder axis 159 and is, by means of the average reduced pressure, securely held on the bottom of the open chamber 151. With the otherwise predetermined dimensions and boundary conditions, the frequency and amplitude of these oscillations can be changed via the pumping power, i.e. can be optimized for the quantitative filling procedure. In particular, during the pure holding time, the pump power can be reduced and only the holding function can be optimized taking into consideration minimum gas through-put. It is also possible to temporarily amplify the shaking procedure prior to the actual filling to thereby "homogenize" the sample substance and level the surface.

The oscillations can be largely harmonic but must not be. Higher harmonics are in fact desirable, which, for example, are produced in that the bottom of the sample vial regularly collides with the bottom of the open chamber 151. In this fashion possible sample substance clumps can be more effectively reduced.

Important parameters which are to be predetermined and optimized are the spring constants of both springs 157, 155 (it is also possible to eliminate spring 155) the diameter of the bore 154 and the width of the ring shaped gap 150. Obviously the general construction of the chambers 151, 152 and the dimensions of the sample vial 19 must be taken into consideration.

The principle dimensions of this concrete embodiment are: length of the opened chamber 151 $l_{151}$=35 mm, diameter of the opened chamber 151 $d_{151}$=16.5 mm, length of the closed chamber 152 $d_{152}$=32.5 mm, diameter of the closed chamber 152 $d_{152}$=11.5 mm, diameter of the bore 154 $d_{154}$=5.5 mm, overall length of the device 15 $l_{15}$=77 mm, diameter of the sphere 156 $d_{156}$=8 mm. Clearly, these values have exemplary character only.

Figure 3:
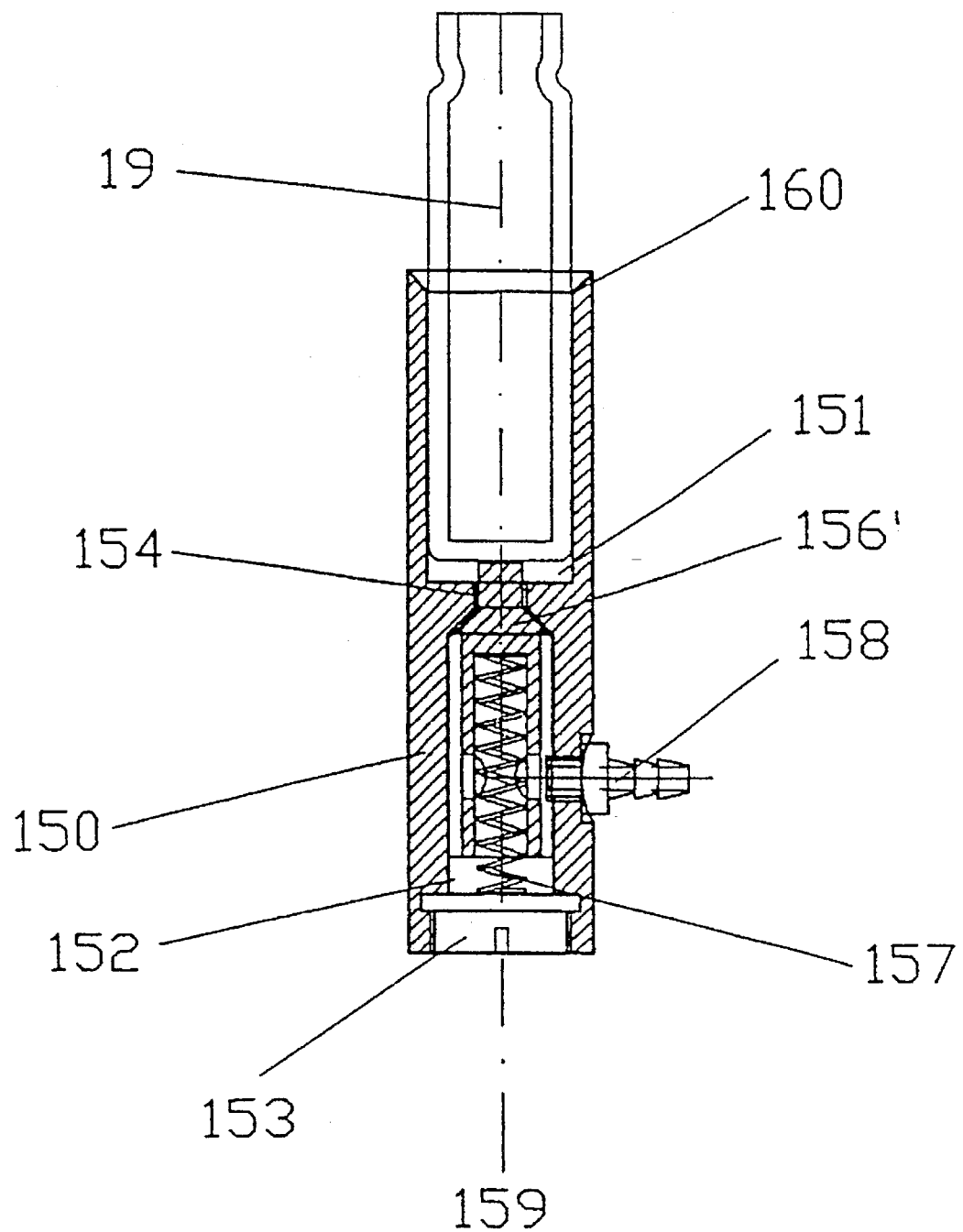
FIG. 3 shows a detailed view of a second embodiment of a shaking and holding device.

FIG. 3 shows a cut through a second embodiment of a shaking and holding device 15 in accordance with the invention. The components, their reference symbols and functions correspond largely to those of FIG. 2. Only the sphere 156 is replace by a striking pin 156' and the spring 155 is not present. In contrast to the sphere 156 the striking pin 156' penetrates through the bore 154 and has direct contact with the bottom of the sample vial 19. The other parameters remain essentially the same, this configuration leads to a greatly reduced suction power requirement for the pump 3. The oscillations are transferred from the oscillating striking pin 156', through mechanical contact, to the bottom of the sample vial 19. These remain, either in constant contact, i.e. the sample vial is constantly pressed onto the striking pin 156' by means of the outside pressure or they become somewhat separated when the sample vial 19 slides outward as a result of which, in a later phase, the vial bottom then strikes the bottom of the chamber or the striking pin strikes the bottom of the bottle. In general, the oscillations are somewhat harder than those in the version of FIG. 2, i.e. they contain more higher harmonics which, in general, is advantageous for the consistency of the filling procedure.

Otherwise statements made in connection with FIG. 2 are correspondingly valid.

Figure 4:
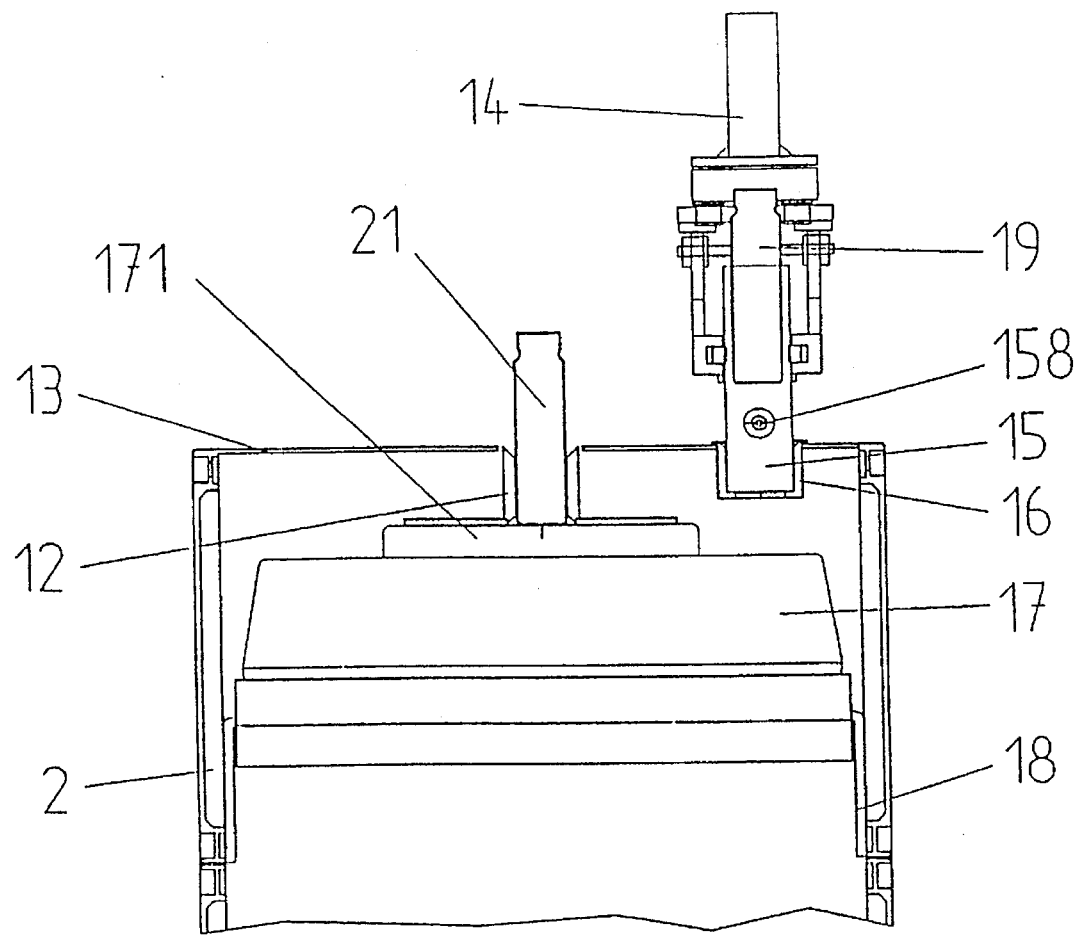
FIG. 4 shows a detailed view of a weighing station with the shaking and holding device in the rest position.

FIG. 4 shows a detailed view of a weighing station. The electronic analysis scale 17 is located in an insert in the housing 2 on a support 18. The guide 12 for a measuring vial 21 located on the measuring table 171 of the scale 17 is fashioned through the housing cover 13. The storage means 16, in which the shaking and holding device 15 is located in its resting position, also enters through the cover 13. It contains a sample vial 19 in its open chamber. The robot grasping arm 14 has grasped the shaking and holding device 15 including the sample vials 19 from above.

Figure 5:
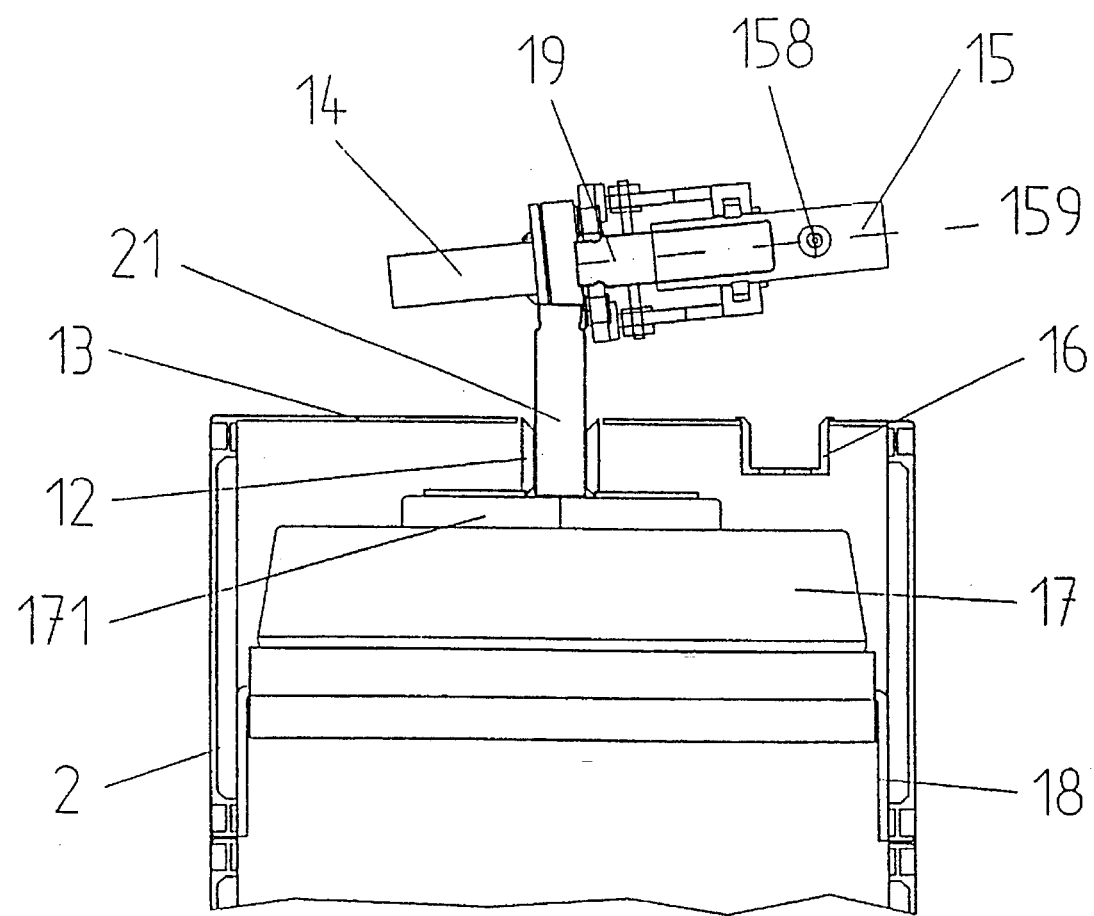
FIG. 5 shows a detailed view of a weighing station with the shaking and holding device in the filling position.

FIG. 5 shows a detailed view of the weighing station, whereby the sample vials 19, located in the filling position, are held by means of the shaking and holding device 15. The shaking and holding device 15, for its part, is held by the robot grasping arm 14. In this position the sample vial, without reduced pressure in the chamber of the shaking and holding device 15, would slide out under the influence of gravity. It is, however, held by same as described in detail above and shaken so that the sample substance and the sample vial 19 can trickle down into the measuring vial 21 in a slow and defined fashion, whereby the electronic analysis scale 17 constantly measures the weight increase.

We claim:

1. A shaking and holding device for the quantitative filling of a powder or granulated sample substance from a sample vessel, comprising an open hollow cylindrical chamber and a closed chamber which are connected by a pressure valve, the open chamber being adapted to accept the sample vessel with close tolerance, so that a ring-shaped gap remains between an inside wall of the open chamber and an outside wall of the sample vessel and further comprising pumping means for activation of the shaking and holding device by pumping on the closed chamber to periodically open and close the pressure valve in response to a pressure decrease and a pressure increase, whereby the pressure increase and decrease set the sample vessel into oscillation, and, suction the sample vessel with an average reduced pressure to hold the sample vessel for pouring into a measuring vessel.

2. The device of claim 1, wherein the pressure valve comprises a separation wall, having a through hole, between the open and the closed chamber and a sphere pressed, by means of a spring within the closed chamber, against the through hole.

3. The device of claim 1, wherein the pressure valve comprises a separation wall, having a through hole, between the open and the closed chamber and a striking pin, pressed by means of a spring within the closed chamber, to penetrate the through hole from the closed chamber into the open chamber for mechanically contacting a bottom of the sample vessel.

4. The device of claim 1, wherein the pumping means comprise a pumping connection on the closed chamber, a suction pump, and a pumping conduit connected between the suction pump and the pumping connection.

* * * * *